United States Patent [19]

Tedeschi

[11] Patent Number: 5,907,109
[45] Date of Patent: May 25, 1999

[54] VEHICLE EMISSION SAMPLING PROBE APPARATUS

[76] Inventor: Rinaldo R. Tedeschi, 11 Trumbull St., Newington, Conn. 06111

[21] Appl. No.: 09/072,950

[22] Filed: May 5, 1998

[51] Int. Cl.⁶ .................................................. G01N 1/00
[52] U.S. Cl. ............................................. 73/864.73
[58] Field of Search ........................ 73/23.31–23.33, 73/863.01–863.03, 863.58, 864.73, 864.34

[56] References Cited

U.S. PATENT DOCUMENTS

| | | | |
|---|---|---|---|
| 2,053,121 | 9/1936 | Vayda | 23/255 |
| 3,284,165 | 11/1966 | Baumann et al. | 23/255 |
| 3,593,023 | 7/1971 | Fullerton et al. | 250/43.5 |
| 3,603,155 | 9/1971 | Morris et al. | 73/23.31 |
| 3,672,225 | 6/1972 | Louis | 73/863.58 |
| 3,917,454 | 11/1975 | Clark | 23/232 R |
| 4,031,747 | 6/1977 | Blanke | 73/23.31 |
| 4,040,783 | 8/1977 | Collin | 23/232 R |
| 4,534,213 | 8/1985 | Mirikidani | 73/118 |
| 4,747,297 | 5/1988 | Okayama et al. | 73/23.33 |
| 4,855,668 | 8/1989 | Crow | 324/65 CR |
| 5,161,417 | 11/1992 | Strong et al. | 73/863.86 |
| 5,216,881 | 6/1993 | Anlauf et al. | 60/276 |
| 5,543,113 | 8/1996 | Koike et al. | 422/83 |

*Primary Examiner*—Robert Raevis
*Attorney, Agent, or Firm*—Schweitzer Cornman Gross & Bondell LLP

[57] ABSTRACT

A vehicle exhaust gas collection probe assembly for the collection of two independent exhaust gas samples from a tailpipe system of a vehicle exhaust system comprises a first collector for collecting an undiluted exhaust gas sample from within the exhaust system and second collection means for collecting the entirety of exhaust gas exiting from an end of the tailpipe system. The second collection means comprises a conical collector having a first open end of a diameter greater than that of the tailpipe system positioned adjacent the end of the tailpipe system and a second end of small diameter coupled to a collection conduit. The first collector comprises a hollow probe having a flexible portion for insertion into the tailpipe system coupled to a conduit positioned along a main longitudinal axis of the conical collector, extending into the conical collector, and being supported by the conical collector.

9 Claims, 2 Drawing Sheets

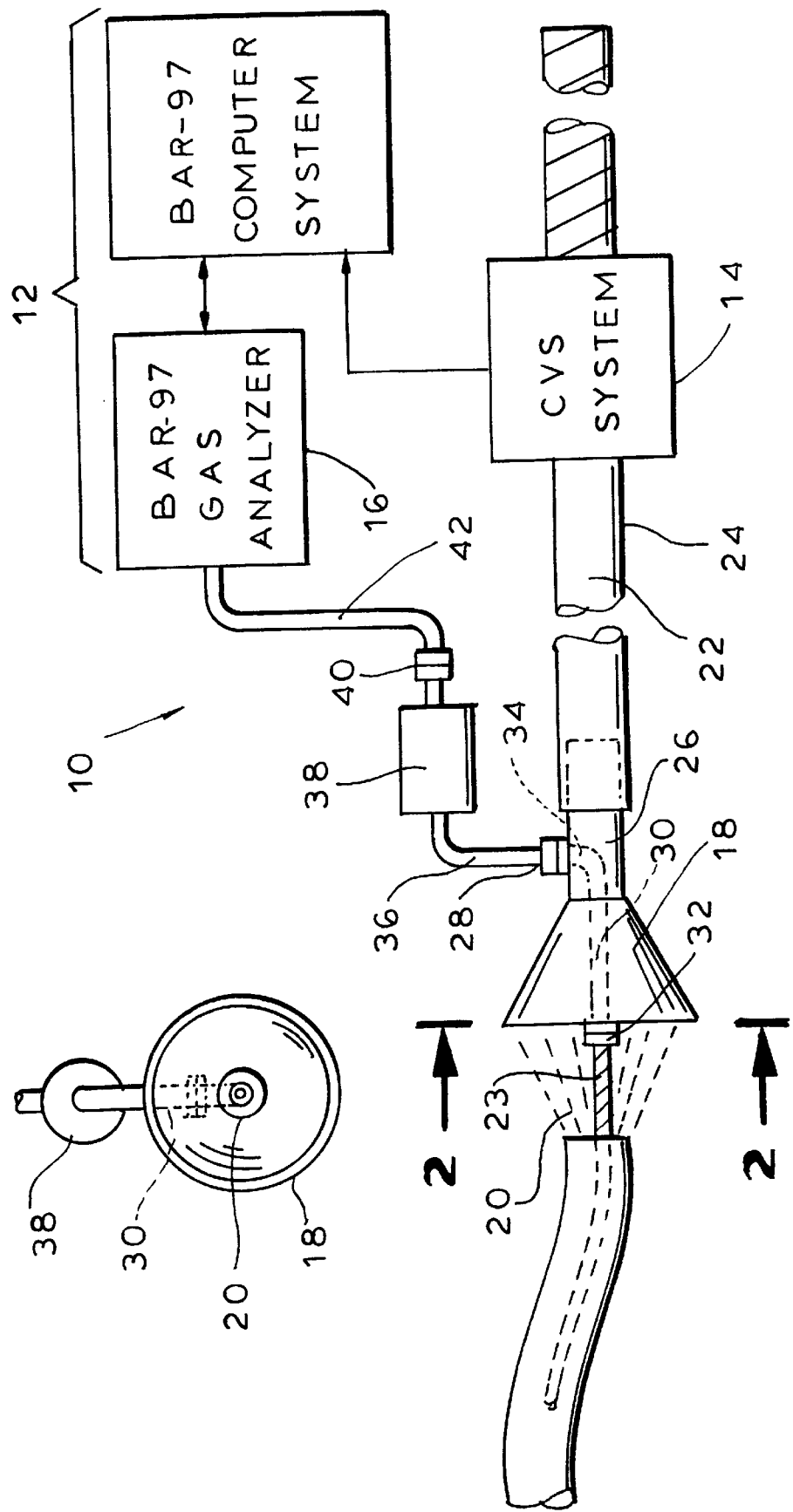

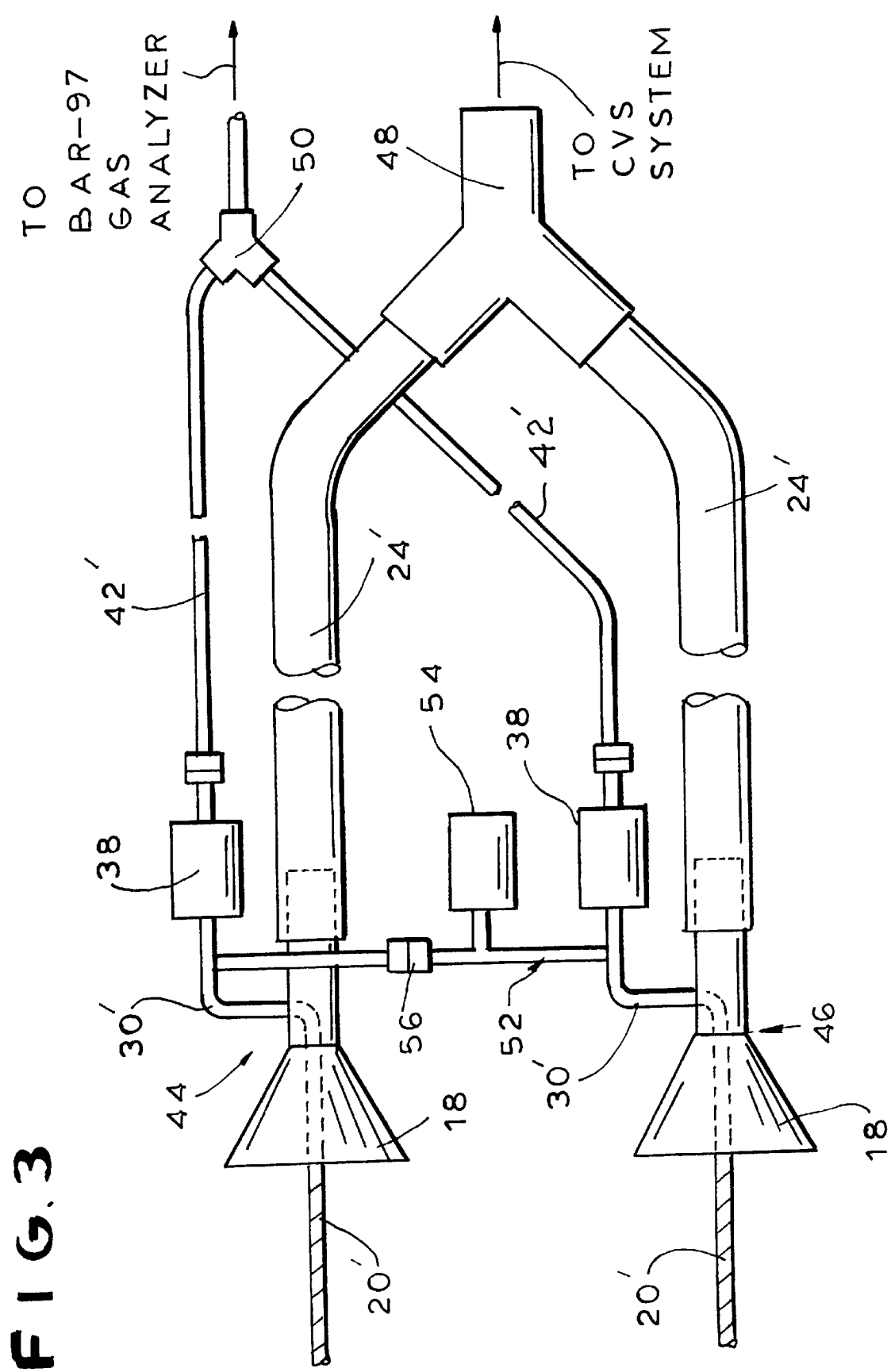

VEHICLE EMISSION SAMPLING PROBE APPARATUS

The present invention relates to a new and improved multi-function sampling probe for use in connection with vehicle exhaust gas analyzers.

BACKGROUND OF THE INVENTION

Exhaust gas analysis plays a significant part in the periodic testing of vehicles required by environmental protection laws and regulations. In addition to exhaust characteristics being demonstrative of engine operating characteristics, allowing the monitoring and measurement thereof, the percentages of particular exhaust gas constituents are subject to guidelines. The state of California has been a leader in establishing such guidelines, the most recent of which are codified in California BAR97 (Bureau of Automotive Repair) regulations.

Different test protocols and exhaust gas analyses require the sampling of the exhaust to be done in alternative manners. For percentage constituent analysis, for example, a small volume of exhaust gas, not contaminated or mixed with ambient air, can be captured and analyzed. This ordinarily requires capture of less than 1% of the tailpipe exhaust. For other tests where exhaust characteristics are reflective of differing engine operating parameters, the total of tailpipe exhaust is required to be sampled, often on an ongoing basis. Because of these differing requirements, the sampling apparatuses employed differ. Traditionally, separate constant volume and free flow collecting probes have been utilized, a test technician manually changing the probes as required during different phases of an integrated test procedure.

The current utilization of separate probes can affect the validity of test results. The manual interchange of probes does not prevent an exhaust sample from a first vehicle being used for one test, and the exhaust from a second vehicle, with a different probe, being used for a second test of a test protocol intended to be carried out for a single specific vehicle. In addition, because of the differing nature of the sampling techniques required, the different probes used are oriented and placed differently with respect to the exhaust system. The use of a plurality of probes, each one being required to be oriented separately and independently, increases the opportunity for improper placement and test error.

It is accordingly a purpose of the present invention to provide an exhaust probe apparatus which is capable of providing differing samples as required by different phases of an integrated vehicle testing protocol.

A further purpose of the present invention is to provide an integrated probe assembly which provides simultaneous independent sample outputs of differing types.

Yet a further purpose of the present invention is to provide a sampling probe which is efficient to use and economical in manufacture.

SUMMARY OF THE INVENTION

In accordance with the foregoing and other objects and purposes, a vehicle exhaust system sampling probe in accordance with the present invention provides first and second sampling probe elements concentrically aligned along a major axis. The first sampling probe is mounted centrally with respect to the axis, and is of an extended flexible construction permitting insertion within the exhaust system tailpipe. The second probe is in the form of a cone, dimensioned to embrace and substantially trap the entirety of the exhaust exiting from the tailpipe. Each of the first and second probes are associated with independent collection means such that the exhaust collected thereby may be analyzed as required.

BRIEF DESCRIPTION OF THE DRAWINGS

A fuller understanding of the present invention will be obtained upon consideration of the following, detailed description of a preferred, but none the less illustrative embodiment thereof, when considered in conjunction with the annexed drawings, wherein:

FIG. 1 is a depiction of a probe system in accordance with the present invention coupled to exhaust gas analysis means;

FIG. 2 is a view taken along line 2—2 of FIG. 1; and

FIG. 3 is a depiction of the invention in an embodiment appropriate for use in connection with dual exhaust system vehicles.

DETAILED DESCRIPTION OF THE INVENTION

As depicted in FIG. 1, the probe apparatus 10 of the present invention is used in connection with an exhaust gas analysis system 12 typically part of an integrated vehicle test system. The exhaust analysis system includes a constant volume sample (CVS) analysis unit 14 as well as a gas analyzer 16 adapted to analyze, for example, a small undiluted exhaust sample with respect to BAR-97 standards which consider the concentration of CO and $CO_2$ in the exhaust. Under such standards, the combined volume percentage of the two gases in an undiluted exhaust sample must be greater than 6 percent by volume. The BAR-97 analysis includes a test for physical integrity of the exhaust system and requires that the sample be taken from an internal point in the exhaust system to avoid dilution effects which may result if the sample is taken near the tailpipe exit. A combined $CO/CO_2$ value below 6 percent by volume indicates that the sample has been diluted by ambient air. Such dilution suggests a leak or misalignment in the exhaust system, allowing ambient air to mix with the exhaust as well as allowing exhaust to exit through the leak. A $CO/CO_2$ value in excess of 6 percent, which represents an average or baseline level of those constituents resulting from normal combustion patterns of gasoline in internal combustion engines, indicates that the exhaust sample being received by the probe is undiluted, indicating system integrity.

The CVS analysis system is utilized for other purposes, as it allows the mass quantity of various components of the exhaust, such as total hydrocarbons, CO, nitrogen oxides and the like, to be measured. An integral requirement of a CVS system is that the total mass flow and any dilution thereto be accounted for. Any dilution not expressly known introduces errors, resulting in incorrect mass measurements. The dilution factor can be determined by inclusion of a known amount of inert gas in the exhaust, or preferably by measuring the concentration of CO and $CO_2$ in a small sample of known volume. This latter methodology is particularly preferred when a BAR97 test series is performed, as $CO/CO_2$ concentration must be determined for the integrity portion of the protocol. In either event, however, it is important that the entirety of the engine exhaust be collected by the CVS system.

It is well established that the operating parameters of an internal combustion engine as utilized in motor vehicles is affected by the back pressure to the combustion chamber generated by the exhaust system. Certainly, one method for collecting the entirety of an exhaust flow is to maintain a physical connection between the end of the exhaust pipe and a collection tube. In addition to difficulties which are associated with establishing a mechanical connection with a tailpipe, which may be of somewhat fragile construction, the direct connection to a pipe leading to an analysis device changes the characteristics of the exhaust system, and may significantly affect the back pressure in the exhaust system, resulting in changes in the operating parameters and characteristics of engine operation. Accordingly, a collection cone is utilized. This cone, as depicted at 18, has an open end of substantially larger diameter than the vehicle tailpipe, and is positioned adjacent, but not physically coupled to, the end of the tailpipe. The CVS system includes a suction pump having a constant flow rate higher than the expected mass flow rate for the tailpipe to insure that all the exhaust can be collected when the cone is in close proximity to the tailpipe end. Ambient air is also collected by the cone and pump as required to maintain the constant flow rate. A correction factor is applied by the CVS system, based upon the $CO/CO_2$ level, inert gas concentration, or other appropriate calculation, to account for the dilution factor produced by the ambient air collected.

As shown in FIG. 1, first probe 20 is of relatively small diameter, able to be inserted within the vehicle tailpipe. The probe may be of a hollow, flexible construction, allowing it to conform to possible undulations of the tailpipe along the inserted distance. The probe may be provided with a series of calibration marks 22 along its length to allow a visual clue to be established regarding the depth of insertion. Typically, an insertion of at least 10 inches is required to insure that a proper sample is being obtained. The probe 20 is coupled to a rigid conduit 30 at 32, which in turn is coupled to the gas analyzer 16.

Probe 20 is positioned to lie substantially along the central axis 22 of sampling cone 18, which in turn is coupled to conduit 24, which leads to CVS analysis unit 14. Cone unit 18 includes a cylindrical coupling portion end 26 which connects in a friction fit with conduit 24. The flared open end 26 of sampling cone 18 is oriented such that flexible first probe 20 extends approximately 15 to 20 inches therebeyond.

The combination of cone 18 and conduit 24 provide the input passageway for the exhaust into CVS system 14. Because of the minimal volume of exhaust collected by probe 20, the simultaneous collection of an undiluted sample thereby does not introduce a meaningful error to the volume of exhaust collected by the cone. The rigid conduit 30 coupled to first probe 20 extends a short distance into the cylindrical portion 26 of cone unit 18, exiting therefrom through its side wall at 28. Typically, rigid conduit 30 may have a first right angle bend 34 to allow exiting through the conduit side wall, and a second right angle bend 36 whereby the conduit then extends away from the probe on an axis essentially parallel to axis 22, and spaced therefrom. An insulated handle 38 may be provided on the rigid conduit to allow the user to support the probe assembly 10 as required. A coupling 40 joins the rigid conduit 30 to sample hose 42 leading to analyzer 16.

By use of the probe assembly 10, both CVS and non-diluted BAR-97-type analyses can be performed simultaneously or consecutively, without the necessity for interchange of sampling devices, thus insuring that the samples required by each test come from a common source. Further, the insertion of the flexible first probe 20 the appropriate distance into the tailpipe automatically positions the cone 18 the necessary distance from the tailpipe end to insure collection of all the exhaust. Test efficiency and reliability is thus significantly enhanced over the use of separate probes which must be interchanged and utilized consecutively.

As depicted in FIG. 3, a dual tailpipe exhaust system may utilize first and second probe systems 44, 46, each of which is configured in accordance with the requirements of the single probe construction of FIGS. 1 and 2. In such a case, the CVS sample conduits 24' are joined together with a Y-fitting 48, the outlet thereof being connected to the CVS analysis unit 14. Similarly, the rigid conduits 30' are each connected to a flexible hose 42' which in turn are led to Y-fitting 50 and thereafter to the BAR-97 analysis unit 16.

As depicted, each of the rigid conduits 30 may be provided with a handle 36. Depending upon the orientation and spacing of the tailpipes, the handles may be held by one or two operators to position the dual flexible probes 20' as required. In addition or alternatively, however, the two probe assemblies 44, 46 may be joined by transverse bar 52 affixed to the two assemblies. The transverse bar may be provided with a central handle 54 which can allow a single operator to more easily support and position the two probes. Transverse bar 48, which may be constructed in two sections, may be provided with an extension and locking assembly 56, as known in the art, to adjust the positioning of the two sections and thus separation of the two probe units to accommodate differing tailpipe orientations.

I claim:

1. A vehicle exhaust gas collection probe assembly for the collection of two independent exhaust gas samples from a tailpipe system of a vehicle exhaust system, comprising first collection means for collecting an undiluted exhaust gas sample from within the exhaust system and second collection means for collecting the entirety of exhaust gas exiting from an end of the tailpipe system, said second collection means comprising a conical collector having a first open end of a diameter larger than that of the end of the tailpipe system positioned adjacent the end of the tailpipe system and a second end coupled to a collection conduit, said conical collector having a main longitudinal axis, said first collection means comprising a hollow probe having a flexible portion for insertion into the tailpipe system coupled to a conduit positioned along said main longitudinal axis, extending into said conical collector, and being supported by said conical collector.

2. The assembly of claim 1 further including a handle to allow the assembly to be positioned with said probe inserted within the tailpipe system and the first open end of the conical collector positioned adjacent the end of the tailpipe system.

3. The assembly of claim 2, wherein the conduit of said first collection means passes through a sidewall of said conical collector, a portion of said conduit exterior to the sidewall forming a portion of said handle.

4. A vehicle exhaust gas collection probe assembly for the collection of two independent exhaust gas samples from a tailpipe system of a vehicle exhaust system having first and second tailpipes each having an end exhausting the exhaust gas into the ambient atmosphere, comprising a first collection system associated with the first tailpipe and a second collection system associated with the second tailpipe, each of said collection systems comprising first collection means for collecting an undiluted exhaust gas sample from a location within the respective tailpipe and second collection means for collecting the entirety of exhaust gas exiting from the end of the respective tailpipe, said second collection means comprising a conical collector associated with the respective tailpipe end, conical collector having a first open end positioned adjacent the respective tailpipe end and of a diameter larger than that of the respective tailpipe end and a second end coupled to a collection conduit, said conduits being joined together to form a single second gas transmission conduit, conical collector having a main longitudinal axis, said first collection means comprising a hollow probes associated with the respective tailpipes, said hollow probe having a flexible portion for insertion into the respective tailpipe coupled to a conduit positioned along the main longitudinal axis of the corresponding conical collector, extending into the respective conical collector, being supported by the respective conical collector, and joined to the other probe conduit to form a single first gas transmission conduit.

5. The assembly of claim 4 further including handle means to allow the assembly to be positioned with said probes inserted within the respective tailpipes and the first open ends of the conical collectors positioned adjacent the end of the respective tailpipe.

6. The assembly of claim 5, wherein the conduit of each of said first collection means passes through a sidewall of the respective conical collector, a portion of said conduit exterior to the sidewall forming a portion of said handle means.

7. The assembly of claim 5 wherein said handle means comprises a transverse bar having first and second ends, said first end supporting said first collection system and said second end supporting said second collection system.

8. The assembly of claim 7 wherein said transverse bar is of adjustable length.

9. The assembly of claim 8 wherein said transverse bar includes a handle located centrally between its first and second ends.

* * * * *